United States Patent [19]

Knifton

[11] Patent Number: 5,003,112
[45] Date of Patent: Mar. 26, 1991

[54] TERTIARY AMYL METHYL ETHER FROM C-5 OLEFIN STREAMS

[75] Inventor: John F. Knifton, Austin, Tex.

[73] Assignee: Texaco Chemical Company, White Plains, N.Y.

[21] Appl. No.: 459,607

[22] Filed: Jan. 2, 1990

[51] Int. Cl.$^5$ .............................................. C07C 41/06
[52] U.S. Cl. ................................................... 568/697
[58] Field of Search ........................................ 568/697

[56] References Cited

U.S. PATENT DOCUMENTS

| | | | |
|---|---|---|---|
| 4,118,425 | 10/1978 | Herbstman | 568/697 |
| 4,193,770 | 3/1980 | Chase et al. | 568/697 |
| 4,204,077 | 5/1980 | Woods et al. | 568/697 |
| 4,605,806 | 8/1986 | Ballantine et al. | 568/697 |
| 4,665,220 | 5/1987 | Gregory et al. | 568/697 |

OTHER PUBLICATIONS

Adams et al, Clays and Clay Minerals, vol. 30, No. 2, 129–134, 1982.

Primary Examiner—Howard T. Mars
Attorney, Agent, or Firm—Jack H. Park; Kenneth R. Priem; Cynthia L. Kendrick

[57] ABSTRACT

A method is disclosed for the preparation of tertiary amyl methyl ether by reaction of methanol and a C-5 olefin over a catalyst comprising an acidic smectite clay, particularly a palladium-modified acidic montmorillonite silica-alumina clay. The method allows for high conversions with yields of up to 93–99 mole %. Further the method is capable of operating efficiently at high LHSVs.

7 Claims, No Drawings

TERTIARY AMYL METHYL ETHER FROM C-5 OLEFIN STREAMS

FIELD OF THE INVENTION

This invention concerns an improved method for the synthesis of tertiary amyl methyl ether by the reaction of methanol and C-5 hydrocarbon streams containing C-5 olefins in the presence of an acidic clay catalyst, particularly montmorillonite acidic silica-alumina clays. The reaction is particularly advantageous in that the tertiary amyl methyl ether (TAME) is generated continuously in up to 53% concentration and isolation of the TAME in as high as 98% purity by fractional distillation has been demonstrated.

BACKGROUND OF THE INVENTION

In the art there is currently interest in using smectite clays as catalysts. It is known that the unique structure permits modifications which provide useful catalyst properties.

In an article titled "Catalysis: Selective Developments", Chem. Systems Report 84-3, 239–249, at Section 3.4320, some of the unusual properties of smectite clays which make them of interest as catalysts are discussed. These compositions are layered and exhibit a 2:1 relationship between tetrahedral and octahedral sites. In addition, the combination of cation exchange, intercalation and the fact that the distance between the layers can be adjusted provide interesting possibilities. In addition, the cations on the interlamellar surfaces ($Ca^{+2}$ or $Na^+$) can be replaced with almost any cation desired by simple ion-exchange techniques.

Art is available which focuses on how various factors affect clay catalysts. In an article titled "Pillared Clays As Catalysts" in *Catal. Rev. Sci. Eng.*, 30(3), 457–499 (1988) there is a discussion of factors affecting the properties of pillared clays, including methods by which the thermal stability can be improved in the range from about 480° C. to about 800° C. It was also found that the method used to dry the flocculated clay appeared to be more important in determining the porosity of the final product than the choice of pillaring agent or the clay layer charge. For example, adsorption is one property which varies with drying method. Also, certain chemicals such as $Al_2O_3$ can be fixed on the clays in order to increase surface area by changing the pore size distribution and increasing thermal stability.

The same article also discusses the acidity of pillared clays as well as ways in which different treatments affect the Lewis or Bronsted sites to a varying extent. It appears to be necessary to invoke the presence of several types of acid sites, because pillared clays do not necessarily function in the same manner as zeolites.

There is a discussion of clay mineral catalysts, including acidic montmorillonite clay catalysts in "Progress in Inorganic Chemistry", Vol. 35, p. 41 (1987). The process of pillaring this type of catalyst is discussed. Pillaring can convert a clay lamellar solid from a material that survives no more than a few hundred degrees centigrade heating before collapsing, into a more heat resistant two dimensional zeolite-type material that can survive heat treatment in moist atmospheres well above 500° C.

In U.S. Pat. Nos. 4,176,090 (1979) and 4,248,739 (1981) Vaughan et al. disclose the addition of a silicate to an aluminum chlorhydral solution to substantially increase the surface area of clays. Some of the best hydrothermal stability reported to date in the art concerns clay intercalated by hydroxy silica-aluminum ions.

It is known in the art that suitably modified smectite clays can be very selective catalysts for a wide range of organic reactions and that they can act as Bronsted and Lewis acids. This is discussed in "Clays as Selective Catalysts in Organic Synthesis", J. M. Adams and K. Martin, *J. of Inclusion Phenomena*, 5, 663 (1987). After surveying the Bronsted acid activity of such clays, Adams et al. found that with cation-exchanged clays, the reactions proceeded below 100° C. provided they involve tertiary or allylic carbocation intermediates. At 150°–180 C. reactions involving primary and secondary carbocations are possible.

The same author discusses the fact that potential Lewis acid centers exist in smectite clays. $Al^{3+}$ and $Fe^{3+}$ ions are normally associated with the octahedral sheets of the montmorillonite. At page 668 there is discussed the reaction of alcohols with isobutene in the presence of montmorillonite catalysts. This reaction gives high yields of the tertiary ether at low temperatures according to the equation:

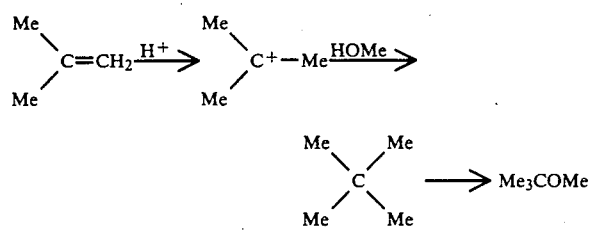

where the rate of reaction was found to be proportional to the isobutene concentration. A plausible reaction scheme is as follows:

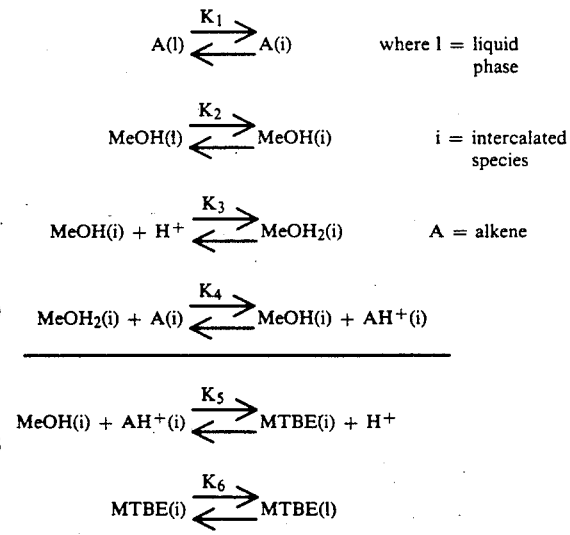

The rate determining step appears to be the protonation of the alkene. Apparently solvent effects can be great, with the use of 1,4-dioxane increasing the rate six-fold and promoting miscibility of all reagents. In contrast, the reaction of alcohols with linear alk-1-enes is slow and gives mixture of alk-2-yl and alk-3-yl ethers.

The use of Group IV Metal Phosphates is discussed in "Recent Advances in Pillared Clays and Group IV Metal Phosphates", A. Clearfield, *Surface Organometal-* lic Chemistry; Molecular Approaches to Surface Catlaysis, 231, 271 (1988). It is known that smectite clays swell with water and are able to exchange large cations such as $[Al_3O_4(OH)_{24}—12H_2O]^{7+}$ and $[Zr(OH)_2.4H_2O]_4^{8+}$. These large cations can then act as pillars to prop open the clay layers. This property allows for the creation of catalyst materials with pores larger than those found in zeolites. In particular there is disclosed the potential use of the layered compound α-zirconium phosphate which is pillared by cross-linking the layers with aryl diphosphonic acid. Where the clay is pillared the pillar spacing apparently is determined by the radius of the ingoing cation.

Smectites characteristically have alumina octahedra sandwiched between layers of silicate tetrahedra. In smectites, substitutions of $Mg^{2+}$ for $Al^{+3}$ and $Li^+$ for $Mg^{2+}$ can take place in the octahedral site or $M^{3+}$ ions can substitute for $Si^{4+}$ in the tetrahedral site.

In J. Am. Chem. Soc., 101. 6891 (1979) Pinnavaia et al. pointed out that the rapid tumbling of simple intercalated ions, such as hydrated $Cu^{2+}$ and $Mn^{2+}$ and movement of free solvent in the clay interlayers indicate the possibility of carrying out metal complex catalyzed reactions in the intra-crystal space of said minerals.

No art has been found suggesting a C-5 raffinate stream could be reacted with a low molecular weight alkanol to synthesize desirable commercial products such as TAME. Synthesis of a product such as tertiary amyl methyl ether by rapid conversion of methanol and a C-5 olefin over an acidic clay would have significant commercial value. Such a process would be particularly efficient if TAME were manufactured as a primary or secondary product from typical C-5 raffinate streams from the production of MTBE, butadiene and light olefins. Furthermore, the acidic clay catalyst described is particularly efficient and thermally stable.

SUMMARY OF THE INVENTION

This invention concerns a process for preparing tertiary amyl methyl ether from methanol and a C-5 olefin over a catalyst comprising an acidic clay catalyst, particularly a montmorillonite acidic silica-alumina clay, at mild temperature and pressure.

A particular advantage of the instant invention over the prior art is that it has been discovered in the instant invention that C-5 raffinate streams from MTBE, butadiene and light olefins can be used to produce TAME. Tertiary amyl methyl ether is useful as an octane enhancer for refiners and in gasoline. In this invention, the TAME can be isolated in as great as 98% purity by fractional distillation.

DESCRIPTION OF THE INVENTION

Preparation of the tertiary amyl methyl ether of this invention may be carried out typically by reacting methanol and a C-5 olefin in the presence of a smectite clay catalyst. The TAME is generated continuously over a catalyst which preferably comprises a montmorillonite acidic silica-alumina clay in powdered, granular or extruded form.

The reaction can be represented by the following:

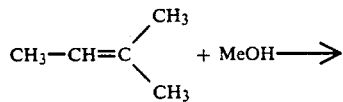 + MeOH ⟶ (Eq. 1)

-continued

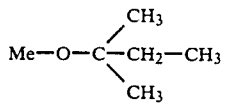

The method is most useful in the reaction of C-5 olefins, particularly those containing a significant quantity of isoamylene. The same method may also be applied to the reaction of other C-5 olefins. For example, the process may be applied to the reaction of a low molecular weight alkanol with 2-methy-1-butene, 2-methyl-2-butene, or 3-methyl-1-butene.

The low molecular weight alkanol may be selected from the group consisting of $C_1$–$C_6$ primary alcohols such as methanol, ethanol, n-propanol and n-hexanol. The examples demonstrate the reaction of methanol and isoamylene.

The catalysts used to effect this reaction are preferably silica and alumina-rich montmorillonite acidic clay catalysts. A variety of clay catalysts containing aluminum and silica are effective in the subject reaction (Eq. 1), however it is necessary that the alumina or silica be acidic under normal operating conditions. As discussed, a group of catalysts which works well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction of Equation 1 are smectite clays. Smectite clays are discussed in the article cited in Chem. Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

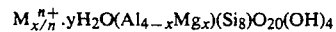

where M represents the interlamellar (balancing cation), normally sodium or lithium and x, y and n are integers.

These montmorillonite clays are best used in the present application in an acidic form. Acids activate montmorillonites by attacking and solubilizing structural cations in the octahedral layers. This opens up the clay structure and increases surface area. These acid treated clays act as strong Bronsted acids.

Acidic montmorillonite clays are the preferred form of smectite clay in the present invention. Said clays may be acidified by treatment with mineral acid. Suitable acids include sulfuric acid and phosphoric acid. Preferably these acid clays should have acidities in the range of 3 to 20, or greater, mg KOH/gm, titrated to a phenolphthalein end point. Their surface area should be >30 m²/g, and preferably 200 to 1000 m²/g. Their moisture content should be limited also, thereby upon heating to 220° F., the weight loss is generally less than 20 wt %.

Illustrative examples of suitable montmorillonite clays include powdered clays such Filtrol Grade 13, 113 and 160, sold by Englehard, clays in granular form, such as Engelhard's granular Clay-24, having a 20/60 mesh size, and grade 25 (10/20 mesh) sold by Englehard, as well as extruded clays such as the Filtrol Clay-62, sold in 1/16" and 3/16" diameter extrudates.

In a further modification of the invention, a transition-metal catalyst, such as platinum or palladium salt, oxide, or complex can be exchanged into the clay, or chemically bonded to the structure of said inorganic support, in order to achieve improved selectivities and yields of desired tertiary amyl methyl ether particularly from mixed C-5 olefin feedstocks. Suitable examples of transition metal derivatives include palladium salts such as palladium chloride, actylacetonate and acetate. Said palladium salts may be introduced into the clay by an ion exchange process, or they may be chemically bonded to a functionalized clay, e.g. an aminosilated clay, such as an aminosilated Engelhard Clay-24 prepared according to the method of Choudary et. al. *J. Mol. Catal.*, 49, L47 (1989). Said authors describe the preparation of an interlamellar montmorillonite-silyamine-palladium(II) catalyst.

An additional possibility is the use of the classes of acidic clay outlined above in combination with a separate heterogeneous transition-metal catalyst. In particular, there is the possibility of employing an acidic clay catalyst in combination with a separate supported palladium or platinum catalyst, for example, a palladium-on-carbon catalyst. Here the support may be carbon, alumina, silica, titania, zirconia, magnesia, as well as combinations thereof. The transition-metal loading should be in the range 0.1 to 20 wt %. Suitable examples include the use of a combination of Engelhard Clay-24 granule[1] with a 5% palladium-on-carbon catalyst. These catalyst combinations may be intimately mixed, or they may be used separately; the weight ratios may vary anywhere from 100:1 to 1:100 or clay-to-Pd catalyst.

Said types of catalyst described could also be used for the cogeneration of MTBE, TAME and higher analogues. Two additional features of said classes of catalyst might be:

(a) The hydrogenation of any diolefin present in the feed stream to monoolefins.
(b) Isomerization of the double bonds of the monoolefin fractions of the same feedstock.

Preparation of tertiary amyl methyl ether may be conducted batchwise, in a continuous slurry bed reactor, or in a fixed-bed, continuous flow, reactor. For practical reasons a fixed bed process is preferred. The catalyst or catalyst combination is effective in the form of a powder, extrudate or granules. In all cases the catalyst concentration should be sufficient to provide the desired catalytic effect.

Preparation of TAME can generally be conducted at temperatures from 20° to 250° C.; the preferred range is 60° to 180° C. The operating pressure may be from zero to 1000 psig, or higher. The preferred pressure range is 100 to 400 psig.

Typically, TAME is generated continuously in up to ca. 53 wt % concentration or higher, in the crude product liquid effluent. The TAME can be isolated in as great as 98% purity by fractional distillation. The olefin feedstock component may be pure isoamylene, a mixture of C-5 olefins (such as a mixture of 2-methyl-1-butene, 2-methyl-2-butene plus 3-methyl-1-butene), a mixture of C-5 olefins plus C-5 alkanes, including a n-pentane and iso-pentane, or a C-5 distillation cut that may comprise hydrocarbons with two, three, four, five, six and higher numbers of carbon atoms per molecule. Said C-5 cut may contain saturated hydrocarbons such as isobutane, n-butane, isopentane, hexanes etc. in combination with olefins such as 1-butene, cis-and trans-2-butene, isobutylene, isoamylene, 3-methyl-1-butene, and 2-methyl-1-butene, plus polyolefins such as 1,3-butadiene and isoprene. Typical feedstocks include a C-5 raffinate stream from an MTBE unit and a C-5 stream from a light olefins unit. Said feedstocks may contain 1 to 50% isoamylene.

The alcohol/C-5 olefin feed can also be diluted with a suitable solvent prior to being fed to the reactor. Suitable diluents include saturated hydrocarbons such as n-pentane, as well as ether-containing solvents such as p-dioxane.

The alcohol to C-5 olefin feed molar ratios may vary from 100:1 to 1:100, but generally a small excess of alcohol is employed. The preferred methanol-to-isoamylene feed molar ratio is 1:1 to 10:1.

Generally methanol and C-5 olefin conversions are good and TAME selectivities, based upon either methanol or isoamylene converted, are often 93-99 mole% or better. Where the C-5 feedstocks are a mixture of C-5 olefins, the TAME selectivities based on isoamylene may exceed 100%. As other C-5 olefin fractions, particularly the 2-methyl-1-butene isomerize and react with the methanol coreactant to form desired product. These selectivities are achieved at total liquid hourly space velocities of 1-10, or greater. Here LHSV is defined as:

$$LHSV = \frac{\text{Weight Of Total Liquid Feed Run Through The Reactor Per Hour}}{\text{Volume of Catalyst In Reactor}}$$

The examples which follow illustrate the preparation of TAME from methanol plus (a) pure isoamylene, (b) isoamylene diluted with n-pentane and (c) a C-5 raffinate stream containing various C-5 olefins including isoamylene. Suitable catalysts for these TAME syntheses illustrated below include:

(1) acidic montmorillonite clays
(2) an acidic montmorillonite clay catalyst containing exchanged palladium salt
(3) a montmorillonite-silylamine-palladium (II) catalyst
(4) a physical mixture of montmorillonite clay plus supported palladium catalyst These examples are only intended as a means of illustration and it should be understood that the invention is not meant to be limited thereby.

Conversion of methanol, or isoamylene, to TAME is estimated in the following examples using equations of the type:

$$\frac{[\text{wt \% conc of isoamylene in feed} - \text{wt \% conc of isoamylene in product}] \times 100}{[\text{wt \% conc of isoamylene in feed}]}$$

Selectivities to TAME are generally estimated from:

$$\frac{\text{Moles of TAME in Product}}{\text{Moles of Methanol (or Isoamylene) Converted}}$$

The attached tabular data illustrate the one-step synthesis of TAME from C-5 olefin plus methanol (e.g. 1). Points which should be noted in the following examples include:

(a) In Example 1, Englehard Clay-24 catalyst was employed to give TAME in VP to 27% concentration when run at LHSV's of 1 to 10 and temperatures in the range 80°-140° C. Here the feed mix comprised pure methanol plus isoamylene in an approximately 2:1 weight ratio (4.8:1 molar ratio).

(b) Where the methanol: isoamylene molar feed ration is 1.2:1, as in Example 2, TAME is generated in up to 53% of the product effluent in 93-99 mole% yields (basis methanol and isoamylene converted respectively). Said TAME may be isolated in 98% purity by fractional distillation.

(c) Where the same 1.2:1 molar mix of methanol/isoamylene is diluted with n-pentane, TAME is again generated in good yields (see Example 3).

(d) TAME production has also been demonstrated where the feedstock is C-5 raffinate stream containing 6.9% isoamylene (see Example 4).

(e) TAME production is similarly demonstrated where the feedstock is a C-5 cut from the light olefins unit containing 14.3% isoamylene (Example 5). In this case the TAME selectivity exceeds 100 mol%, indicating that other C-5 olefin components in this feed mix are being etherified to give tertiary amyl methyl ether.

(f) TAME production is also demonstrated with a palladium-modified montmorillonite clay. Selectivities to TAME are very good (Example 6).

(g) Selectivity to TAME is further raised to 264 mole% (Basis apparent isoamylene conversion) where the catalyst is a mix of acidic montmorillonite clay plus 5% palladium-on-carbon (Example 7, compare with Example 5). This result indicates still more of the other C-5 olefin components in the feed are being etherified to give the desired tertiary amyl methyl ether.

(h) Where the 1.2:1 molar mix of methanol plus isoamylene is diluted with n-pentane (Example 8), a palladium-on-aminosilanated clay also generates TAME.

EXAMPLE 1

This example illustrates the synthesis of t-amyl methyl ether from isoamylene and methanol using an acidic clay catalyst.

The syntheses were conducted in a a tubular reactor (0.563" id, 12" long), constructed of 316 stainless steel, operated upflow and mounted in a furnace, controllable to ±1.0° C. and fitted with pumps allowing flow control to < +1 cc/hr. The reactor was also fitted with a pressure regulating device and equipment for monitoring temperature, pressure and flow rate.

The reactor was charged at the beginning of the experiment with 25 cc of Engelhard Clay-24 granules. A screen of glass beads was placed at the top and bottom of the reactor to ensure the clay granules would remain in the middle portion.

The catalyst bed was first conditioned overnight by washing with methanol/isoamylene (2:1) mix at 100° C., 300 psi back pressure and a liquid flow rate of 25 cc/hr. The same solution of methanol+isoamylene (2:1, weight ration) was then pumped through the catalyst bed at 25 cc/hr, while the reactor was held at 100° C. at a total pressure of 300 psi. Samples of the product were taken periodically, by collecting on-stream in a 316 ss pressure bomb. Typical analyses data for samples taken under these conditions are summarized in Table I.

Catalyst performance over a range of temperatures (80°-140° C.) and liquid flow rates (25-250 cc/hr. LHSV's 1-10) was also measured, after reaching equilibrium conditions. Summary data for these additional six runs are also given in Table I.

A sample of the composite effluent (1744 g) was fractionally distilled at atmospheric pressure. A distillate fraction (233 g) boiling at ca. 85°-86° C. comprise >96% tertiary amyl methyl ether (TAME).

TABLE II

TAME FROM MeOH/ISOAMYLENE (4.8:1) - I

Catalyst: Clay-24
Feed %: MeOH 68.7; C$_5$H$_{10}$ - 31.2

| Temp. (°C.) | Flow (cc/hr) | Sample | MeOH | C$_5$OH | C$_5-$ | TAME | Day |
|---|---|---|---|---|---|---|---|
| 100 | 25 | 1 | 66.4 | 11.6 | 0.2 | 21.7 | 1 |
|  |  | 2 | 59.1 | 13.3 | 0.1 | 27.4 | 2 |
|  |  | 3 | 58.7 | 13.5 | 0.1 | 27.8 |  |
| 120 | 25 | 4 | 59.2 | 14.1 | 0.1 | 26.5 | 3 |
|  |  | 5 | 58.9 | 14.1 | 0.3 | 26.5 |  |
|  |  | 6 | 59.6 | 13.9 | 0.1 | 26.3 | 4 |
|  |  | 7 | 59.0 | 14.2 | 0.1 | 26.6 |  |
| 140 | 25 | 8 | 60.4 | 17.7 | 0.1 | 21.0 | 5 |
|  |  | 9 | 60.4 | 17.6 | 0.1 | 21.0 |  |
|  |  | 10 | 60.6 | 17.7 | 0.1 | 20.7 | 6 |
|  |  | 11 | 60.4 | 17.6 | 0.1 | 21.1 |  |
| 80 | 25 | 12 | 62.8 | 21.0 | 0.1 | 16.1 | 7 |
|  |  | 13 | 62.8 | 21.0 | 0.1 | 16.2 |  |
|  |  | 14 | 63.5 | 19.9 | 0.1 | 16.4 | 8 |
|  |  | 15 | 62.8 | 21.2 | 0.1 | 15.9 |  |
| 100 | 25 | 16 | 59.8 | 13.7 | 0.1 | 26.4 | 9 |
|  |  | 17 | 58.9 | 13.8 | 0.1 | 27.2 |  |
| 100 | 100 | 18 | 60.0 | 16.7 |  | 23.2 | 10 |
|  |  | 19 | 60.1 | 16.8 | 0.1 | 23.0 |  |
| 100 | 250 | 20 | 62.8 | 22.1 | 0.1 | 15.1 | 11 |
|  |  | 21 | 62.8 | 22.2 | 0.1 | 14.9 |  |

EXAMPLE 2

Following the procedures of Example 1, a fresh sample of Clay-24 granular catalyst was treated with a 1.2:1 molar mixture of methano. (768 g) and isoamylene (1402 g) at 100° C. using a flow rate of 25 cc/hr. Samples of the product effluent were taken on-stream periodically and analyzed by GLC. Results are summarized in Table II.

Again catalyst performance was investigated over a range of temperatures (80°-140° C.) and liquid flow rates (25-100 cc/hr). Summary data for these additional runs are also given in Table II.

A sample of the composite effluent (989 g) was fractionally distilled at atmospheric pressure. A distillate fraction (127 g) boiling at ca. 85° C. comprised 98% TAME.

An analysis of the data from Sample #4 shows:

| | |
|---|---|
| Isoamylene conversion | 57% |
| Methanol conversion | 48% |
| TAME selectivity (basis isoamylene) | >99 mole % |
| TAME selectivity (basis methanol) | 93 mole % |

TABLE II

TAME FROM MeOH/ISOAMYLENE (1.2:1) - III
Catalyst: Clay-24
Feed %: MeOH 36.8; C$_5$H$_{10}$ - 63.1

| Temp. (°C.) | Flow (cc/hr) | Sample | PRODUCT COMPOSITION (%) | | | Day |
|---|---|---|---|---|---|---|
| | | | MeOH | C$_5$H$_{10}$ | TAME | |
| 100 | 25 | 1 | 23.8 | 26.5 | 48.7 | 1 |
| | | 2 | 20.7 | 27.8 | 50.2 | |
| | | 3 | 19.8 | 27.0 | 52.8 | 2 |
| | | →4 | 19.0 | 27.1 | 53.6 | |
| 120 | 25 | 5 | 22.7 | 32.7 | 44.1 | 3 |
| | | 6 | 22.2 | 33.8 | 43.8 | |
| 140 | 25 | 7 | 25.5 | 39.4 | 34.1 | 4 |
| | | 8 | 25.5 | 40.3 | 31.5 | |
| 80 | 25 | 9 | 25.4 | 38.1 | 35.7 | 5 |
| | | 10 | 23.6 | 39.7 | 36.7 | |
| 100 | 100 | 11 | 20.0 | 29.7 | 50.3 | 6 |
| | | 12 | 20.4 | 30.6 | 49.0 | |

EXAMPLE 3

Following the procedures of Example 1, a fresh sample of Clay-24 granular catalyst (40 cc) was treated with a 2:1 molar mixture of methanol/isoamylene diluted with n-pentane at 80° C. using a flow rate of 80 cc/hr. Samples of the product effluent were taken on-stream periodically and analyzed by GLC. Results are summarized in Table III.

Again catalyst performance was investigated over a range of temperatures (60°-120° C.). Summary data for these additional runs are also given in Table III.

An analysis of the data from Sample #5 shows:

| | |
|---|---|
| Isoamylene conversion | 51% |
| Methanol conversion | 39% |
| TAME selectivity (basis methanol) | 95 mole % |

TABLE III

TAME FROM MeOH/ISOAMYLENE (1.2:1) - VI
Catalyst: Clay-24
Feed %: MeOH 10.0; C$_5$H$_{10}$ 17.7; C$_5$H$_{12}$ 71.4.

| Temp. (°C.) | Flow (cc/hr) | Sample | PRODUCT COMPOSITION (%) | | | | Day |
|---|---|---|---|---|---|---|---|
| | | | MeOH | C$_5$H$_{10}$ | C$_5$H$_{12}$ | TAME | |
| 80 | 80 | 1 | 8.1 | 13.6 | 70.7 | 5.9 | 1 |
| | | 2 | 8.1 | 13.7 | 71.1 | 5.4 | |
| | | 3 | 7.9 | 13.3 | 71.1 | 6.0 | 2 |
| | | 4 | 7.3 | 14.0 | 71.7 | 5.2 | |
| 100 | 80 | →5 | 6.1 | 8.6 | 71.0 | 11.8 | 3 |
| | | 6 | 6.1 | 8.8 | 71.1 | 11.6 | |
| 120 | 80 | 7 | 6.4 | 10.5 | 71.0 | 8.8 | 4 |
| | | 8 | 6.9 | 10.6 | 71.0 | 8.8 | |
| 60 | 80 | 9 | 9.7 | 17.6 | 71.2 | 0.7 | 5 |
| | | 10 | 9.8 | 17.4 | 71.3 | 0.7 | |

EXAMPLE 4

Following the procedures of Example 1, a fresh sample of granular Clay-24 catalyst (40 cc) was treated with a mixture of C-5 raffinate (3000 g) from a MTBE unit, containing about 6.9% isoamylene, plus methanol (320 g) at 80 C using a flow rate of 80 cc/hr. Samples of the product effluent were taken on-stream periodically and analyzed by GLC for C-5 and TAME content. Results are summarized in Table IV.

Catalyst performance was checked over a range of operative temperatures (80°-120° C.) and flow rates (40-80 cc/hr). Summary data for these additional runs may also be found in Table IV.

TABLE IV

TAME FROM MeOH/C-5 RAFFINATE
Run 6472-50
Catalyst: Clay-24

| Temp. (°C.) | Flow (cc/hr) | Sample | Liquid Composition (%) | | | | | | Total Sample | |
|---|---|---|---|---|---|---|---|---|---|---|
| | | | C-4 Olefins | | | | | | | |
| | | | 1— | ISO— | CIS-2 | TRANS-2 | 3-Me-1 | 2-Me-2 | MeOH | TAME |
| | | F | 2.7 | 0.2 | 3.2 | | 2.5 | 6.9 | 8.3 | 0.3 |
| 80 | 80 | 1 | 0.6 | | 3.2 | 2.7 | 2.5 | 6.5 | 6.5 | 1.0 |
| | | 2 | 0.6 | 0.1 | 3.3 | 2.8 | 2.5 | 5.7 | 8.4 | 1.5 |
| 100 | 80 | 3 | 2.7 | 0.1 | 3.3 | | 2.5 | 4.7 | 7.4 | 3.6 |
| | | 4 | 2.8 | 0.1 | 3.3 | | 2.6 | 4.8 | 7.6 | 3.9 |
| 120 | 80 | 5 | 0.6 | 0.2 | 3.1 | | 2.5 | 4.9 | 7.7 | 2.4 |
| | | 6 | 0.6 | 0.3 | 3.1 | | 2.4 | 5.1 | 7.4 | 2.2 |
| 100 | 40 | 7 | 2.6 | 0.1 | 3.1 | | 2.5 | 4.7 | 8.6 | 3.8 |
| | | 8 | 2.7 | 0.1 | 3.2 | | 2.5 | 4.7 | 8.6 | 3.8 |
| 120 | 40 | 9 | 0.6 | 0.2 | 3.0 | 2.6 | 2.4 | 5.0 | 8.6 | 2.7 |
| | | 10 | 0.6 | 0.2 | 3.1 | 2.6 | 2.4 | 5.0 | 8.2 | 2.6 |

EXAMPLE 5

Following the procedures of Example 1, a fresh sample of granular Clay-24 catalyst (40 cc) was treated with a mixture of C-5 cut (3000 g) from a light olefin unit, containing about 14.3% isoamylene, plus methanol (640 g) at 80° C. using a flow rate of 80 cc/hr. Samples of the product effluent were taken on-stream periodically and analyzed by GLC, GLC-ir and GLC-m.s. for C-5 and TAME content. Results are summarized in Table V.

Again catalyst performance was checked over a range of operating temperatures (80°-120° C.) and flow rate (40-80 cc/hr).

An analysis of the data from Sample #3 shows:

| | |
|---|---|
| Apparent isoamylene conversion | 43% |
| Methanol conversion | 51% |
| TAME selectivity (basis isoamylene) | 124 mole % |

TABLE V

TAME FROM MeOH/ C-5 CUT

Catalyst Clay-24

| Temp. (°C.) | Flow (cc/hr) | Sample | Liquid Composition (%) | | | | | | | | | |
|---|---|---|---|---|---|---|---|---|---|---|---|---|
| | | | C-5 Fraction C-4 Olefins | | | | | | | | Total Sample | |
| | | | 1— | ISO— | CIS-2 | TRANS-2 | $C_4^{2-}$ | 3-Me | 2-Me-2 | 2-Me-1 | MeOH | TAME |
| | | F-1 | 0.9 | 0.6 | 3.0 | 5.3 | 6.7 | 30.2 | 14.3 | 4.0 | 22.4 | — |
| 80 | 80 | 1 | 0.9 | 0.2 | 3.2 | 5.6 | 7.4 | 32.8 | 9.4 | 1.3 | 14.2 | 7.2 |
| | | 2 | 0.9 | 0.1 | 3.3 | 5.7 | 7.4 | 32.8 | 9.1 | 1.2 | 12.7 | 7.5 |
| 100 | 80 | →3 | 0.9 | 0.1 | 3.3 | 5.8 | 7.7 | 33.9 | 8.1 | 1.2 | 10.9 | 8.8 |
| | | 4 | 0.9 | 0.1 | 3.2 | 5.6 | 7.4 | 32.7 | 7.9 | 1.2 | 11.6 | 8.7 |
| 120 | 80 | 5 | 0.9 | 0.1 | 3.3 | 5.7 | 7.7 | 32.7 | 9.6 | 1.8 | 12.0 | 6.2 |
| | | 6 | 0.9 | 0.2 | 3.3 | 5.7 | 7.7 | 32.6 | 9.5 | 1.8 | 12.0 | 6.2 |
| 100 | 40 | 7 | 1.0 | 0.1 | 3.5 | 5.9 | 7.8 | 33.7 | 8.3 | 1.2 | 12.0 | 8.7 |
| | | 8 | 1.0 | 0.1 | 3.5 | 6.0 | 7.7 | 33.4 | 8.2 | 1.2 | 11.4 | 8.7 |
| 120 | 40 | 9 | 1.0 | 0.2 | 3.4 | 6.0 | 7.8 | 32.1 | 10.0 | 1.7 | 15.2 | 7.0 |
| | | 10 | 1.0 | 0.1 | 3.4 | 6.0 | 7.8 | 32.0 | 10.0 | 1.7 | 15.4 | 7.2 |
| 80 | 80 | 11 | 1.0 | 0.2 | 3.3 | 5.9 | 7.5 | 31.0 | 10.6 | 1.9 | 13.7 | 5.6 |
| | | 12 | 1.0 | 0.2 | 3.3 | 6.0 | 7.5 | 31.0 | 10.6 | 1.9 | 13.4 | 5.8 |

EXAMPLE A

To a 50 g sample of Engelhard Clay-24 granules was added a solution of palladium acetylacetonate (1.5 g 5 mmole) in absolute ethanol (200 cc). The mixture was stirred slowly at 55° C. for 6 hrs, filtered, and the solids washed with ethanol and dried overnight in vacuo at 40° C.

The recovered grey solids (48 g) were found to contain 0.2% Pd.

EXAMPLE B

To a 1 liter flask was added 11.5 g of dichlorobis (benzonitrile) palladium(II) (30 mmole), 100 g of aminosilanated Clay-24 (prepared according to the literature method) and 500 g of dried toluene. The mixture was stirred at ambient temperature for 24 hours, filtered, and the solids first washed with dried toluene then extracted with toulene for 8 hrs. The filtered solids were again washed with toulene and dried in vacuo at 40° C.

The recovered grey solids (108 g) were found to contain 2.7% Pd and 1.2% N.

EXAMPLE 6

Following the procedures of Example 1, a sample of palladium-modified montmorillonite clay (25 cc) prepared according to the procedure of Example A, was treated with a mix of methanol plus isoamylene over a range of operating temperatures (80°-120° C.) and flow rates (25-200 cc/hr, LHSV =1-8). Samples of the product effluent were taken on-stream periodically and analyzed by GLC. Results are summarized in Table VI.

An analysis of the date from sample #2 shows:

| | |
|---|---|
| Concentration of TAME in the crude product effluent | 53% |
| TAME selectivity (basis methanol) | 90 mole % |
| TAME selectivity (basis isoamylene) | >99 mole % |

TABLE VI

TAME FROM MeOH/ISOAMYLENE (1.2:1)

Catalyst: Pd-Modified Clay-24
Feed %: MeOH 38.2; $C_5H_{10}$ 61.7.

| Temp. (°C.) | Flow (cc/hr) | Sample | PRODUCT COMPOSITION (%) | | | Day |
|---|---|---|---|---|---|---|
| | | | MeOH | $C_5H_{10}$ | TAME | |
| 100 | 25 | 1 | 19.7 | 28.4 | 50.9 | 1 |
| | | →2 | 19.6 | 27.4 | 53.0 | 2 |
| | | 3 | 19.1 | 27.6 | 53.1 | |
| 80 | 25 | 4 | 24.3 | 37.7 | 37.9 | 3 |
| | | 5 | 24.3 | 38.2 | 37.5 | |
| 120 | 25 | 6 | 46.6 | 23.8 | 29.6 | 4 |
| | | 7 | 23.6 | 34.1 | 41.8 | |
| 100 | 100 | 8 | 21.9 | 31.5 | 46.7 | 5 |
| | | 9 | 21.9 | 31.8 | 46.2 | |
| | 200 | 10 | 24.1 | 36.1 | 39.8 | 6 |
| | | 11 | 24.2 | 36.1 | 39.6 | |

EXAMPLE 7

Following the procedures of Example 1, 40 cc of a physical mixture of Engelhard Clay-24 granules (30 g) plus a 5% palladium-on-carbon granules (10 g) was charged to the reactor, then treated with a liquid feed of C-5 cut (3000 g) containing 13.1 wt % isoamylene and 48.3 wt % component of 3-methyl-1-butene, 2-methyl-2-butene and 2-methyl-1-butene, plus methanol (640 g) over a range of temperatures (80°-180° C.). Samples of the product effluent were taken on-stream periodically and analyzed by GLC and by GLC-iv. Results are summarized in Table VII.

An analysis of the data from Sample #6 shows:

| | |
|---|---|
| Concentration of TAME in the crude effluent | 8.9% |
| Apparent isoamylene conversion | 22% |
| TAME selectivity (basis isoamylene) | 264 mole % |

TABLE VII

TAME FROM MeOH/ C-5 CUT

Catalyst Clay-24 + Pd/C

| Temp. (°C.) | Flow (cc/hr) | Sample | Liquid Composition (%) | | | | | | | | Total Sample | |
|---|---|---|---|---|---|---|---|---|---|---|---|---|
| | | | C-5 Fraction C-4 Olefins | | | | | | | | | |
| | | | 1— | ISO— | CIS-2 | TRANS-2 | $C_4^{2-}$ | 3-Me | 2-Me-2 | 2-Me-1 | MeOH | TAME |
|  |  | F-1 | 0.6 | 0.4 | 2.4 | 4.1 | 0.1 | 30.4 | 13.1 | 4.8 | 21.2 | — |
| 80 | 80 | 1 | 0.6 | 0.4 | 2.5 | 4.3 | 0.1 | 31.4 | 12.7 | 3.8 | ? | −1.2 |
|  |  | 2 | 0.6 | 0.3 | 2.5 | 4.3 | 0.1 | 31.6 | 12.7 | 3.7 | 19.9 | 1.7 |
| 100 | 80 | 3 | 0.7 | 0.1 | 2.6 | 4.4 | 0.1 | 33.1 | 10.9 | 2.0 | 16.8 | 6.8 |
|  |  | 4 | 0.7 | 0.2 | 2.6 | 4.5 |  | 32.9 | 10.9 | 2.0 | 16.7 | 7.3 |
| 120 | 80 | 5 | 0.7 | 0.1 | 2.6 | 4.5 |  | 33.9 | 10.2 | 1.5 | 16.0 | 8.7 |
|  |  | → 6 | 0.7 | 0.1 | 2.7 | 4.6 | 0.1 | 33.7 | 10.2 | 1.5 | 16.1 | 8.9 |
|  |  | F-2 | 0.6 | 0.4 | 2.4 | 4.2 | 0.1 | 30.6 | 13.1 | 4.8 | 19.5 | — |
| 140 | 80 | 7 | 0.7 | 0.1 | 2.8 | 4.8 |  | 32.7 | 10.8 | 1.6 | 15.8 | 7.9[b] |
|  |  | 8 | 0.7 | 0.1 | 2.7 | 4.7 |  | 32.8 | 10.8 | 1.6 | 16.0 | 7.7 |
| 160 | 80 | 9 | 0.7 | 0.2 | 2.6 | 4.6 |  | 29.9 | 12.9 | 2.5 | 13.8 | 4.5 |
|  |  | 10 | 0.7 | 0.2 | 2.5 | 4.4 |  | 30.8 | 13.1 | 2.7 | 17.3 | 3.9 |
| 180 | 80 | 11 | 0.7 | 0.2 | 2.4 | 4.3 |  | 29.3 | 13.5 | 2.4 | 11.4 | 3.2[c] |
|  |  | 12 | 0.7 | 0.3 | 2.5 | 4.4 |  | 30.3 | 13.3 | 2.6 | 19.5 | 2.3 |

EXAMPLE 8

Following the procedure of Example 1, a sample of palladium-on an aminosilated montmorillonite clay (40 cc) prepared according to the procedure of Example B, was treated with a mix of methanol and isoamylene diluted with n-pentane over a range of temperatures (60°–140° C.). Samples of the product effluent were taken in-stream and analyzed by GLC. Results are summarized in Table VIII.

An analysis of the data from Sample #7 shows:

| Isoamylene conversion | 41% |
|---|---|
| TAME selectivity (basis isoamylene) | 79% |

TABLE VIII

TAME FROM MeOH/ISOAMYLENE

| Temp. (°C.) | Flow (cc/hr) | Sample | PRODUCT COMPOSITION (%) | | | | Day |
|---|---|---|---|---|---|---|---|
| | | | MeOH | $C_5$ | $C_{5-}$ | TAME | |
|  |  | F-1 | 9.4 | 69.7 | 17.1 | — |  |
| 60 | 80 | 1 | 8.5 | 71.8 | 17.2 | 0.1 | 1 |
|  |  | 2 | 8.3 | 70.7 | 16.9 | 0.1 |  |
| 80 | 80 | 3 | 9.1 | 71.1 | 15.7 | 1.2 | 2 |
|  | 80 | 4 | 10.9 | 71.0 | 14.8 | 1.3 |  |
| 100 | 80 | 5 | 10.5 | 68.4 | 11.2 | 6.3 | 3 |
|  | 80 | 6 | 10.1 | 69.2 | 12.4 | 5.3 |  |
| 120 | 80 | → 7 | 7.7 | 69.1 | 10.1 | 8.1 | 4 |
|  | 80 | 8 | 8.2 | 68.6 | 10.1 | 7.7 |  |
| 140 | 80 | 9 | 9.8 | 68.6 | 11.4 | 5.0 | 5 |
|  | 80 | 10 | 9.7 | 69.4 | 11.6 | 4.5 |  |

What is claimed is:

1. A method for preparation of tertiary amyl methyl ether comprising reacting methanol and a C-5 olefin over an acidic smectite clay catalyst modified with palladium at a temperature of about 20° C. to 250° C. and a pressure of from zero to 1000 psig.

2. The method of claim 1 wherein the palladium-modified smectite clay is prepared by ion-exchange of a palladium salt with said smectite clay.

3. The method of claim 1 where the palladium-modified smectite clay is prepared by palladium salt addition to an aminosilated smectite clay.

4. The methods of claims 2 or 3 wherein said palladium salt is selected from the group consisting of palladium(II) acetylacetonate, palladium chloride and palladium acetate.

5. The method of claim 1 wherein the acidic clay catalyst is physically mixed with a supported palladium catalyst.

6. The method of claim 5 wherein the supported palladium catalyst has a support selected from the group consisting of carbon, alumina, silica and mixtures thereof.

7. The method of claim 6 wherein the supported palladium catalyst is a 5% palladium-on-carbon catalyst.

* * * * *